US010285935B2

(12) United States Patent
Garbuzova-Davis et al.

(10) Patent No.: US 10,285,935 B2
(45) Date of Patent: May 14, 2019

(54) NON-INVASIVE METHOD FOR DIRECT DELIVERY OF THERAPEUTICS TO THE SPINAL CORD IN THE TREATMENT OF SPINAL CORD PATHOLOGY

(71) Applicants:Svitlana Garbuzova-Davis, Tampa, FL (US); Cesario Venturina Borlongan, Tampa, FL (US); Harry Ronald van Loveren, Tampa, FL (US); Peter Richard Nelson, Tampa, FL (US)

(72) Inventors: Svitlana Garbuzova-Davis, Tampa, FL (US); Cesario Venturina Borlongan, Tampa, FL (US); Harry Ronald van Loveren, Tampa, FL (US); Peter Richard Nelson, Tampa, FL (US)

(73) Assignees: University of South Florida, Tampa, FL (US); United States Department of Veterans Affairs, Washington, DC (US)

( * ) Notice: Subject to any disclaimer, the term of this patent is extended or adjusted under 35 U.S.C. 154(b) by 0 days.

(21) Appl. No.: 15/384,808

(22) Filed: Dec. 20, 2016

(65) Prior Publication Data

US 2017/0173307 A1 Jun. 22, 2017

Related U.S. Application Data

(60) Provisional application No. 62/270,873, filed on Dec. 22, 2015.

(51) Int. Cl.
*A61K 9/00* (2006.01)
*A61M 25/10* (2013.01)

(52) U.S. Cl.
CPC .......... *A61K 9/0019* (2013.01); *A61K 9/0085* (2013.01); *A61M 25/1011* (2013.01);
(Continued)

(58) Field of Classification Search
CPC .............. A61M 25/1011; A61M 25/10; A61M 2025/1015; A61M 2025/1052
See application file for complete search history.

(56) References Cited

U.S. PATENT DOCUMENTS 4,404,971 A * 9/1983 LeVeen .............. A61B 17/1204
604/101.05
4,573,966 A * 3/1986 Weikl ................. A61M 25/1011
604/101.05

(Continued)

OTHER PUBLICATIONS

Sanberg, et al., Navigating cellular repair for the central nervous system. Clin Neurosurg. 2008;55:133-137.

(Continued)

*Primary Examiner* — Bradley J Osinski
*Assistant Examiner* — Nilay J Shah
(74) *Attorney, Agent, or Firm* — Michele L. Lawson; Smith & Hopen, P.A.

(57) ABSTRACT

Most spinal cord therapies are administered systemically, with only a small portion of the therapeutic reaching the spinal cord. A novel method for delivering therapeutics directly to the spinal cord is provided. The method uses a dual balloon catheter to isolate the microvasculature around a region of the spinal cord. Once isolated, one or more therapeutics are delivered directly to the spinal cord blood supply. This allows for smaller, safer therapeutic dose to be utilized.

4 Claims, 3 Drawing Sheets

(52) U.S. Cl.
CPC ............... *A61M 2025/1015* (2013.01); *A61M 2025/1052* (2013.01)

(56) References Cited

U.S. PATENT DOCUMENTS

| | | | | |
|---|---|---|---|---|
| 5,925,016 A * | 7/1999 | Chornenky | ............ | A61M 25/09 604/19 |
| 6,358,536 B1 * | 3/2002 | Thomas | ................. | A61K 31/00 424/608 |

OTHER PUBLICATIONS

Willing, et al., Routes of stem cell administration in the adult rodent. Methods in Mol Biol. 2008;438:383-401.
Hess & Borlongan, Stem cells and neurological diseases. Cell Prolif. Feb. 2008;41 Suppl 1:94-114.
Ehrhart, et al., Distribution of infused human umbilical cord blood cells in Alzheimer's disease-like murine model. Cell Transplant. Sep. 25, 2015; PMID 26414627.
Garbuzova-Davis, et al., Intravenous administration of human umbilical cord blood cells in a mouse model of amyotrophic lateral sclerosis: distribution, migration, and differentiation. J Hematother Stem Cell Res. Jun. 2003;12 (3):255-270.
Garbuzova-Davis, et al., Multiple intravenous administrations of human umbilical cord blood cells benefit in a mouse model of ALS. PLoS ONE. 2012;7(2):e31254.
Garbuzova-Davis, et al., Human umbilical cord blood treatment in a mouse model of ALS: optimization of cell dose. PLoS ONE. 2008;3(6):e2494.
Garbuzova-Davis, et al., Transplantation of human umbilical cord blood cells benefits an animal model of Sanfilippo syndrome type B. Stem Cells Dev. Aug. 2005;14(4):384-9394.
Garbuzova-Davis, et al., Intravenous administration of human umbilical cord blood cells in an animal model of MPS IIIB. J Comp Neurol. Jul. 1, 2009;515(1):93-101.
Willing, et al., Repeated administrations of human umbilical cord blood cells improve disease outcomes in a mouse model of Sanfilippo syndrome III B. Cell Transplant. 2014;23(12):1613-1630.
Vendrame, et al., Infusion of human umbilical cord blood cells in a rat model of stroke dose-dependently rescues behavioral deficits and reduces infarct volume. Stroke. Oct. 2004;35(10):2390-2395.
Vendrame, et al., Cord blood rescues stroke-induced changes in splenocyte phenotype and function. Exp Neural. May 2006; 199(1):191-200.
Zawadzka, et al., Lack of migration and neurological benefits after infusion of umbilical cord blood cells in ischemic brain injury. Acta Neurobiol Exp (Wars). 2009;69(1):46-51.
Makinen, et al., Human umbilical cord blood cells do not improve sensorimotor or cognitive outcome following transient middle cerebral artery occlusion in rats. Brain Res. Dec. 6, 2006;1123(1):207-215.
Acosta, et al., Intravenous bone marrow stem cell grafts preferentially migrate to spleen and abrogate chronic inflammation in stroke. Stroke. Sep. 2015;46(9):2616-2627.
Lee, et al., Differential migration of mesenchymal stem cells to ischemic regions after middle cerebral artery occlusion in rats. PLoS ONE 2015;10(8):e0134920.
Du, et al., Intra-arterial delivery of human bone marrow mesenchymal stem cells is a safe and effective way to treat cerebral ischemia in rats. Cell transplant. 2014;23 Suppl 1:S73-82.
Mitkari, et al., Intra-arterial infusion of human bone marrow-derived mesenchymal stem cells results in transient localization in the brain after cerebral ischemia in rats. Exp Neurol. Jan. 2013;239:158-162.
Toyoshima, et al., Intra-arterial transplantation of allogeneic mesenchymal stem cells mounts neuroprotective effects in a transient ischemic stroke model in rats: analyses of therapeutic time window and its mechanisms. PLoS ONE. 2015;10(6):e0127302.
Gao, et al., The dynamic in vivo distribution of bone marrow-derived mesenchymal stem cells after infusions. Cells tissues Organs. 2001;169(1):12-20.
Li, et al., Intravenous transplantation of allogeneic bone marrow mesenchymal stem cells and its directional migration to the necrotic femoral head. Int J Med Sci. 2011;8(1):74-83.
Meyerrose, et al., In vivo distribution of human adipose-derived mesenchymal stem cells in novel xenotransplantation models. Stem Cells. Jan. 2007;25(1):220-227.
Zhang, et al., In vivo tracking of neuronal-like cells by magnetic resonance in rabbit models of spinal cord injury. Neural Regen Res. Dec. 25, 2013;8(36):3373-3381.
Tan, et al., Neuroprotective effect of methylprednisolone combined with placenta-derived mesenchymal stem cell in rabbit model of spinal cord injury. Int J Clin Exp Pathol. 2015;8(8):8976-8982.

* cited by examiner

NON-INVASIVE METHOD FOR DIRECT DELIVERY OF THERAPEUTICS TO THE SPINAL CORD IN THE TREATMENT OF SPINAL CORD PATHOLOGY

FIELD OF INVENTION

This invention relates to methods to deliver focused pharmaceutical compositions for treating neurological diseases. Specifically, the invention provides for a catheter for isolation and administration of compositions to selected neurons affected by a neurological disease.

BACKGROUND OF THE INVENTION

Current treatment of motor neuron disorders, such as ALS, spinal cord injury, spinal cord stroke, or spinal cord ischemia, is mainly ineffective due to the non-selective, systemic and often indirect nature of cell or drug delivery. Numerous pre-clinical studies on development of stem cell-based therapies for neurodegenerative disorders or other pathological conditions primarily focus on system (intravenous) routes of cell transplantation (Sanberg, et al., Navigating cellular repair for the central nervous system. Clin Neurosurg. 2008; 55:133-137; Willing, et al., Routes of stem cell administration in the adult rodent. Methods Mol Biol. 2008; 438:383-401; Hess & Borlongan, Stem cells and neurological diseases. Cell Prolif. 2008 February; 41 Suppl 1:94-114; Ehrhart, et al., Distribution of infused human umbilical cord blood cells in Alzheimer's disease-like murine model. Cell Transplant. 2015 Sep. 25; PMID 26414627). Though there have been some promising results, there are significant limitations due to cell migration to CNS tissue, specifically in the spinal cord, possible due to the non-selective and often indirect nature of cell delivery. In a mouse model of amyotrophic lateral sclerosis (ALS), a single repeated IV injection of human umbilical cord blood cells (hUCBCs) resulted in wide distribution of cells within and outside the CNS (Garbuzova-Davis, et al., Intravenous administration of human umbilical cord blood cells in a mouse model of amyotrophic lateral sclerosis: distribution, migration, and differentiation. J Hematother Stem Cell Res. 2003 June; 12(3):255-270; Garbuzova-Davis, et al., Multiple intravenous administrations of human umbilical cord blood cells benefit in a mouse model of ALS. PLoS ONE. 2012; 7(2):e31254). While some cells were found in the brain and spinal cord, most cells were distributed in the peripheral organs, mainly the spleen. Other studies optimizing hUCBC doses for ALS treatment showed toxicity at the highest IV dose ($50 \times 10^6$), similar to graft-versus-host disease (Garbuzova-Davis, et al., Human umbilical cord blood treatment in a mouse model of ALS: optimization of cell dose. PLoS ONE. 2008; 3(6):e2494). A study of hUCBC treatment of the metabolic disorder MPS IIIB showed limited cell migration into the brain of knockout mice modeling the disease after either lateral cerebral ventricle (Garbuzova-Davis, et al., Transplantation of human umbilical cord blood cells benefits an animal model of Sanfilippo syndrome type B. Stem Cells Dev. 2005 August; 14(4):384-9394) or IV cell infusion (Garbuzova-Davis, et al., Intravenous administration of human umbilical cord blood cells in an animal model of MPS IIIB. J Comp Neurol. 2009 Jul. 1; 515(1):93-101; Willing, et al., Repeated administrations of human umbilical cord blood cells improve disease outcomes in a mouse model of Sanfilippo syndrome type III B. Cell Transplant. 2014; 23(12):1613-1630).

In middle cerebral artery occlusion (MCAO) rat models of ischemic stroke, though IV administration of hUCBC at different doses showed benefits in behavior recovery, and reduced brain infarct volumes, the transplanted cells mainly congregated in the spleen (Vendrame, et al., Infusion of human umbilical cord blood cells in a rat model of stroke dose-dependently rescues behavioral deficits and reduces infarct volume. Stroke. 2004 October; 35(10):2390-2395; Vendrame, et al., Cord blood rescues stroke-induced changes in splenocyte phenotype and function. Exp Neurol. 2006 May; 199(1):191-200). Other studies have shown no effect on neurological deficit or infarct volume after IV transplant of hUCBC, attributed to a lack of cell migration to the ischemic tissue (Zawadzka, et al., Lack of migration and neurological benefits after infusion of umbilical cord blood cells in ischemic brain injury. Acta Neurobiol Exp (Wars). 2009; 69(1):46-51; Makinen, et al., Human umbilical cord blood cells do not improve sensorimotor or cognitive outcome following transient middle cerebral artery occlusion in rats. Brain Res. 2006 Dec. 6; 1123(1):207-215). A recent study has found human bone marrow stromal cells, when IV administered into chronic post-stroke rats, migrated to the spleen, but not the brain (Acosta, et al., Intravenous bone marrow stem cell grafts preferentially migrate to spleen and abrogate chronic inflammation in stroke. Stroke. 2015 September; 46(9):2616-2627), while another study showed IV administration of bone marrow-derived mesenchymal stem cells (BM-MSCs). In early post-stroke rats was associated with better functional recovery and cell migration to the cortex (Lee, et al., Differential migration of mesenchymal stem cells to ischemic regions after middle cerebral artery occlusion in rats. PLoS ONE. 2015; 10(8):e0134920). Other studies have demonstrated that intra-arterial (IA) administration of human BM-MSCs is more efficient than IV administration in treating cerebral ischemia in rats (Du, et al., Intra-arterial delivery of human bone marrow mesenchymal stem cells is a safe and effective way to treat cerebral ischemia in rats. Cell transplant. 2014; 23 Suppl 1:S73-82; Mitkari, et al., Intra-arterial infusion of human bone marrow-derived mesenchymal stem cells results in transient localization in the brain after cerebral ischemia in rats. Exp Neurol. 2013 January; 239:158-162), due to direct cell migration to ischemic areas of the brain. Moreover, IA cell administration into MCAO rats at 24 hours post-stroke provides better functional recovery and reduction of infarct volumes (Toyoshima, et al., Intra-arterial transplantation of allogeneic mesenchymal stem cells mounts neuroprotective effects in a transient ischemic stroke model in rats: analyses of therapeutic time window and its mechanisms. PLoS ONE. 2015; 10(6):e0127302).

In a study analyzing in vivo distribution of rat BM-MSCs administered into syngenic rats via IV or IA routes, MSCs were detected primarily in the lungs, followed by the liver, then other organs, after both types of administration (Gao, et al., The dynamic in vivo distribution of bone marrow-derived mesenchymal stem cells after infusions. Cells tissues Organs. 2001; 169(1):12-20). Another study investigating feasibility of allogenic GFP-labeled BM-MSCs via IV transplantation in a rabbit model of femoral head necrosis showed cell migration to the lungs, liver, bone marrow, normal and necrotic femoral heads (Li, et al., Intravenous transplantation of allogeneic bone marrow mesenchymal stem cells and its directional migration to the necrotic femoral head. Int J Med Sci. 2011; 8(1):74-83). Administration of human adipose-derived mesenchymal cells into sublethally irradiated immune-deficient mice via IV, intraperitoneal, or subcutaneous routes showed cell distribution in multiple tissues across the various routes (Meyerrose, et al., In vivo distribution of human adipose-derived mesenchymal stem cells in novel xenotransplantation models. Stem Cells. 2007 January; 25(1):220-227). These results indicate multiple homing cites for transplanted cells and the likelihood that cell distribution is deleteriously influenced by indirect administration.

In a rabbit spinal cord injury model, rabbit BM-MSCs induced into neuronal-like cells were transplanted into the subarachnoid space and shown to migrate to the spinal cord injury region and improve functional recovery (Zhang, et al., In vivo tracking of neuronal-like cells by magnetic resonance in rabbit models of spinal cord injury. Neural Regen Res. 2013 Dec. 25; 8(36):3373-3381). A similar neuroprotective effect was observed after injection of placenta-derived mesenchymal stem ells into injured rabbit spinal cord (tan, et al., Neuroprotective effect of methylprednisolone combined with placenta-derived mesenchymal stem cell in rabbit model of spinal cord injury. Int J Clin Exp Pathol. 2015; 8(8):8976-8982). Although some benefits of local cell transplant have been observed, possible Wallerian degeneration of axons distal form the lesion may obstruct full motor recovery. Despite intensive investigations of various treatment options for spinal cord injury/motor neuron disorders, current stem cell-based therapeutics for the pathological spinal cord have limited efficacy. Additionally, systemic intravenous or parenchymal administration of therapeutics provides limited distribution or cell migration within the spinal cord in various animal models of disease, leading to inadequate efficacy, inefficient utilization of costly resources, and significant risk for systemic toxicity. As a result, despite intense investigation, current stem cell-based therapeutics for spinal cord disorders have shown limited benefit.

As such, the inventive method provides direct stem cell transplantation into the spinal cord thereby significantly improving efficiency of delivery and successful uptake of the cells in target tissues that will lead to better therapeutic outcomes compared to systemic delivery. The present device and methods are envisioned useful for pharmacotherapies, as well as existing cell-based therapies, and gene therapies. Furthermore, localized cell delivery into the spinal cord, as opposed to systemic infusion, will require a much smaller dose of therapeutics and be more cost effective. Thus, direct administration of stem cells and other therapeutic agents to the spinal cord addresses the shortcomings of prior administration methods by providing concentrated, site-directed delivery to target tissues. This method will improve treatment options for motor neuron degenerative diseases, such as perioperative spinal cord ischemia, ALS, spinal cord injury, spinal cord stroke, or other spinal cord ischemia.

This invention consists of a novel non-invasive method for direct delivery of therapeutics (stem cells or drugs) to the spinal cord in the treatment of spinal cord pathology. Using fluoroscopic imaging, a guide wire would be inserted via percutaneous stick into the femoral artery and then threaded up into the vertebral arteries; once in place, a dual balloon catheter would be guided to a point above the segmental cervical spinal arteries (i.e. ascending cervical, anterior spinal artery, anterior radicular artery) and used to segmentally occlude the vessel and prevent blood access to the brain during injection of therapeutics. The catheter has infusion ports between the two occlusion balloons which would allow for injection of therapeutics directly into the segmental spinal arteries without risking brain or systemic exposure. Once the therapeutic agents have been delivered selectively to the spinal cord, the balloon would be deflated and removed. This same approach could also be used to occlude and isolate segments of the thoracic or abdominal aorta to deliver therapeutics through segmental thoracic or lumbar spinal arteries to more selectively target disease processes in these regions.

Using this novel technique, therapeutics of interest could be selectively delivered to a discrete region of the spinal cord to increase efficacy of treatment and minimize intracranial or systemic exposure. This invention has multiple applications in treatment of neurodegenerative disorders such as Amyotrophic Lateral Sclerosis (ALS), traumatic spinal cord injury, spinal cord stroke, and perioperative spinal cord ischemia during vascular procedures.

Systemic intravenous administration of therapeutics provides limited cell or drug distribution within the spinal cord in various animal models of disease, leading to limited efficacy and the utilization of inefficiently and costly high dosages with significant risk for systemic toxicity. The novel method described here will allow a selective, safe and effective, non-invasive approach to treating specific spinal cord disorders. An additional benefit of this method will be the avoidance of superfluous cell or drug distribution to non-spinal cord areas with resulting toxicity. Moreover, localized delivery into the spinal cord, as opposed to systemic infusion (as in the case of intravenous approach), will require a much smaller dose of therapeutics to afford efficacy. This invention might prompt improved therapies for a wide range of neurodegenerative and ischemic disorders.

BRIEF DESCRIPTION OF THE DRAWINGS

For a fuller understanding of the invention, reference should be made to the following detailed description, taken in connection with the accompanying drawings, in which.

DETAILED DESCRIPTION OF THE INVENTION

Figures 1, 2:
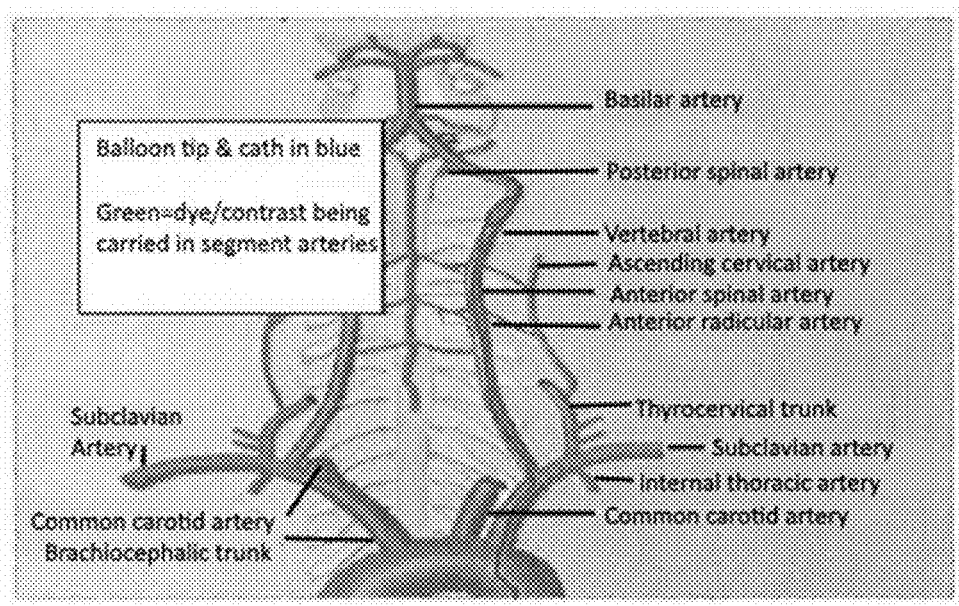
FIG. 1 is an image showing a schematic representation of selected deliver of therapeutics to a discrete region of the spinal cord. A wire is initially inserted via percutaneous stick into the femoral artery, then threaded up into the vertebral artery.
FIG. 2 an image showing a schematic representation of the catheter envisioned for use in the methods described herein.

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

The present invention is a device and method for treating a neurological disorder. The novel minimally-invasive intra-arterial method of therapeutic delivery presented herein is based on selective blood vessel catheterization and isolation, providing significantly enhanced delivery of stem cells directly into a target region of the spinal cord, while concurrently avoiding cell distribution to non-spinal cord areas. The ability of the inventive technique to target selected spinal cord regions provides numerous advantages, including (1) improving delivery of existing therapies, and (2) developing new treatments for spinal cord pathologies.

As the therapeutic was delivered directly to the patient intra-arterially, stem cells (SCs) were used as an ideal cell population and transplant and engraftment in the spinal cord microvasculature. This is in part due to the reduced risk of graft-versus-host immune response present with SCs.

Pharmaceutical compositions of the present invention may comprise the active agent, i.e., a compound or composition comprising a spinal cord therapeutic, such as SCs, alone or may include the active agent and any suitable additional component, such as one or more pharmaceutically acceptable carriers, diluents, adjuvants, excipients, or vehicles, such as preserving agents, fillers, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Each carrier is preferably acceptable in the sense of being compatible with the other ingredients of the formulation and not injurious to the patient.

Dosage unit forms of a pharmaceutical composition of the present invention comprise a desired amount of the active agent per dose unit and, if intended for oral administration, can be in the form, for example, of a tablet, a caplet, a pill, a hard or soft capsule, a lozenge, a cachet, a dispensable powder, granules, a suspension, an elixir, a dispersion, or any other form reasonably adapted for such administration. If intended for parenteral administration, it can be in the form, for example, of a suspension or transdermal patch. If intended for rectal administration, it can be in the form, for example, of a suppository. In one embodiment, the dosage unit form is a discrete dose form such as a tablet or a capsule suitable for oral administration, each containing a predetermined amount of the active agent.

Excipients employed in the compositions of the present invention may be solids, semi-solids, liquids or combinations thereof. In one embodiment, the excipient(s) is/are solids. Compositions of the invention containing excipients can be prepared by any known technique that comprises, for example, admixing an excipient with the composition.

Compositions of the invention optionally comprise one or more pharmaceutically acceptable carriers or diluents as excipients. Suitable carriers or diluents illustratively include, but are not limited to, either individually or in combination, lactose, including anhydrous lactose and lactose monohydrate; starches, including directly compressible starch and hydrolyzed starches (e.g., Celutab™ and Emdex™); mannitol; sorbitol; xylitol; dextrose (e.g., Cerelose™ 2000) and dextrose monohydrate; dibasic calcium phosphate dihydrate; sucrose-based diluents; confectioner's sugar; monobasic calcium sulfate monohydrate; calcium sulfate dihydrate; granular calcium lactate trihydrate; dextrates; inositol; hydrolyzed cereal solids; amylose; celluloses including microcrystalline cellulose, food grade sources of alpha- and amorphous cellulose (e.g., RexcelJ), powdered cellulose, hydroxypropylcellulose (HPC) and hydroxypropylmethylcellulose (HPMC); calcium carbonate; glycine; bentonite; block co-polymers; polyvinylpyrrolidone; and the like. Such carriers or diluents, if present, may constitute in total about 5% to about 99%, about 10% to about 85%, or even about 20% to about 80%, of the total weight of the composition. The carrier, carriers, diluent, or diluents selected may exhibit suitable flow properties and, where tablets are desired, compressibility.

Compositions of the invention optionally comprise one or more pharmaceutically acceptable disintegrants as excipients, particularly for tablet formulations. Suitable disintegrants include, but are not limited to, either individually or in combination, starches, including sodium starch glycolate {e.g., Explotab™ of PenWest) and pregelatinized corn starches {e.g., National™ 1551 of National Starch and Chemical Company, National™ 1550, and Colorcon™ 1500), clays {e.g., Veegum™ HV of R.T. Vanderbilt), celluloses such as purified cellulose, microcrystalline cellulose, methylcellulose, carboxymethylcellulose and sodium carboxymethylcellulose, croscarmellose sodium (e.g., Ac-Di-Sol™ of FMC), alginates, crospovidone, and gums such as agar, guar, locust bean, karaya, pectin and tragacanth gums.

Disintegrants may be added at any suitable step during the preparation of the composition, particularly prior to granulation or during a lubrication step prior to compression. Such disintegrants, if present, may constitute in total about 0.2% to about 30%, about 0.2% to about 10%, or even about 0.2% to about 5%, of the total weight of the composition.

Pharmaceutical formulations of the invention can be administered simultaneously or sequentially with other drugs or biologically active agents. Examples include, but are not limited to, antioxidants, free radical scavenging agents, peptides, growth factors, antibiotics, bacteriostatic agents, immunosuppressives, anticoagulants, buffering agents, anti-inflammatory agents, anti-pyretics, time-release binders, anesthetics, steroids and corticosteroids.

Preferred unit dosage formulations are those containing a daily dose or unit, daily subdose, or an appropriate fraction thereof, of an agent. Therapeutic amounts can be empirically determined and will vary with the condition being treated, the subject being treated, and the efficacy and toxicity of the agent. Similarly, suitable dosage formulations and methods of administering the agents can be readily determined by those of ordinary skill in the art.

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

The rabbits were anesthetized. A dual balloon catheter was inserted into the common femoral artery via percutaneous micropuncture and guided up the femoral artery into the iliac artery, into the descending aorta, and into the carotid artery using ultrasound. A 4-F sheath (COOK Medical, Bloomington, Ind.) was placed, and the catheter inserted. A fluoroscopic imaging device (OEC 9000 Elite Mobile C-arm Imaging System, GE Healthcare, Buckinghamshire, UK) was used to visualize a guide wire, which was advanced through the abdominal and thoracic aortae and selectively placed in the vertebral artery, as seen in FIG. 1. Upon placement of the guide wire, a 2.5F CXI microcatheter (COOK) was placed for diagnostic imaging to delineate the segmental spinal cord perfusion. The 2.5F catheter was exchanged for a 4F multiport isolation-infusion catheter with dual balloons spaced 4 cm apart and infusion holes between the balloons (Vascular Designs, Inc., San Jose, Calif.), as seen in FIG. 2. The catheter was positioned to encompass the feeding vessels, i.e. ascending cervical, anterior spinal artery, anterior radicular artery, to the target cervical spinal cord distribution. The balloons were gently inflated to isolate the arterial segment, typically for 10-15 seconds, and injection of a contrast agent confirmed selective isolation was accomplished. The selective isolation-infusion strategy allows for direct delivery to the target spinal cord segment(s), while preventing blood/infusion to the brain.

Figure 3:
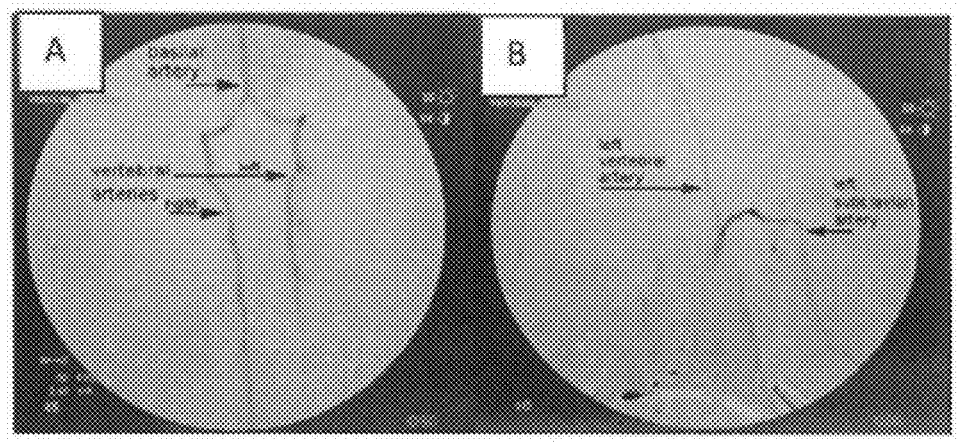
FIG. 3A is a fluoroscopic image of vertebral arteries in a rabbit. Injection of contrast agent via the femoral artery into rabbits clearly showed vertebral arteries on both sides of the animal.
FIG. 3B is a fluoroscopic image of vertebral arteries in a rabbit. Injection of contrast agent via the femoral artery into rabbits showed the left side of the spinal cord.
Figure 4:
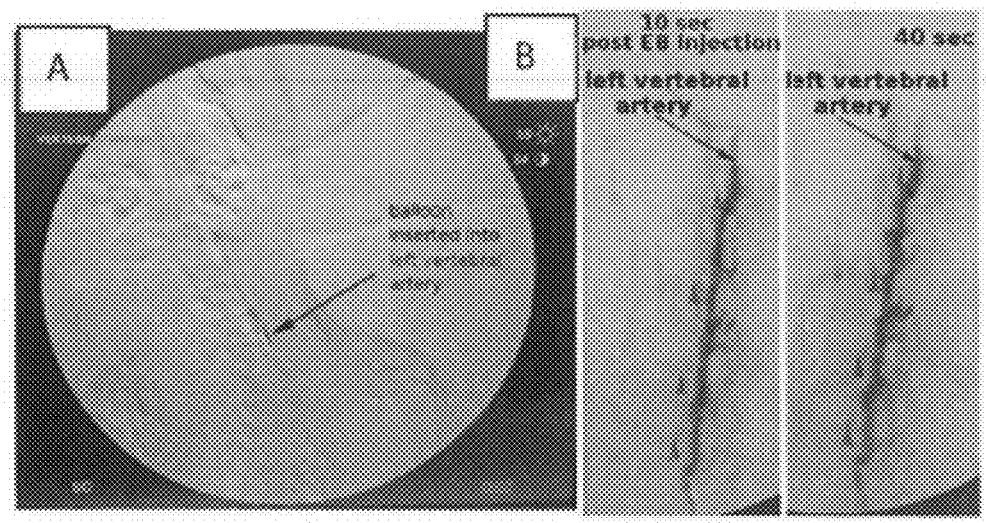
FIG. 4A is a fluoroscopic image of vertebral arteries in a rabbit with the dual balloon catheter in place.
FIG. 4B is a fluoroscopic image of vertebral arteries in a rabbit with the dual balloon catheter in place. Injection of contrast agent/dye at 10 sec and 40 sec.

To test the selective isolation of the present method, a contrast agent was injected into the femoral artery using the 2.5 F microcatheter. Imaging of the both sides of the spinal cord, seen in FIG. 3A, and the right side, seen in FIG. 3B, clearly show the vertebral and basilar and subclavian arteries. Insertion of the 4 F isolation-infusion catheter to a point above the segmental cervical spinal arteries, as seen in FIG. 4A, confirmed the location of the catheter. After the balloons were inflated, selected isolation and infusion was confirmed using 5 ml Evans Blue dye, injected through the catheter directly into the left vertebral artery. Angiographically, the dye distributed to the segmental spinal arteries in the rabbit's cervical spinal cord with more significant appearance at 40 sec after injection, as seen in FIG. 4B.

Figure 5:
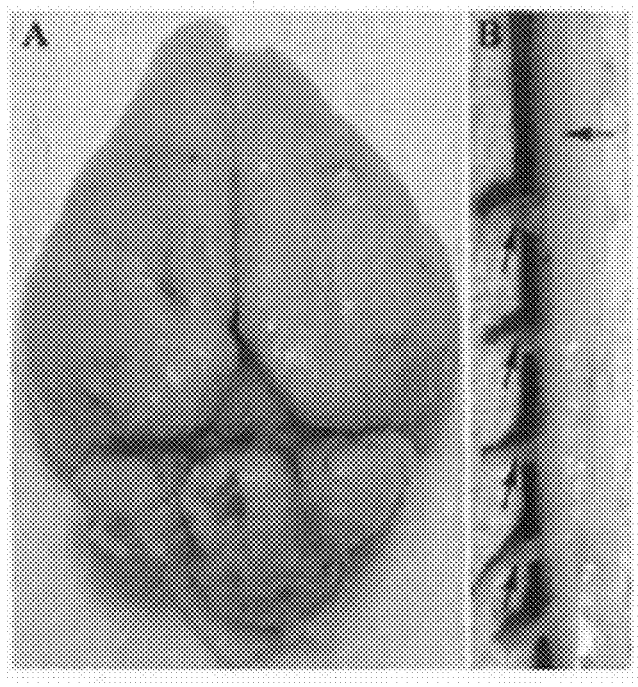
FIG. 5 is a gross image of the brain and cervical spinal ford from a rabbit after EB injection. A) No EB dye was seen in the brain whereas B) EB (dark staining) was seen within the cervical segment and in dorsal root ganglions (arrows) on the left side of the spinal cord (injection site).

After dye injection, balloon deflation, and catheter removal, restoration of blood flow was observed and rabbits were sacrificed 15 min later by $CO_2$ inhalation. Rabbits were then transcardially perfused under pressure to deliver 0.1M PB, followed by 4% PFA in 0.1M PB at 85 mm Hg. The brain and cervical spinal cord were removed and fixed in 4% PFA in 0.1M PB. Selective infusion was tested by analyzing presence of Evans Blue dye. As seen in FIG. 5, lack of staining in the brain and limited staining on the cervical spinal cord confirmed selective infusion.

Figure 6:
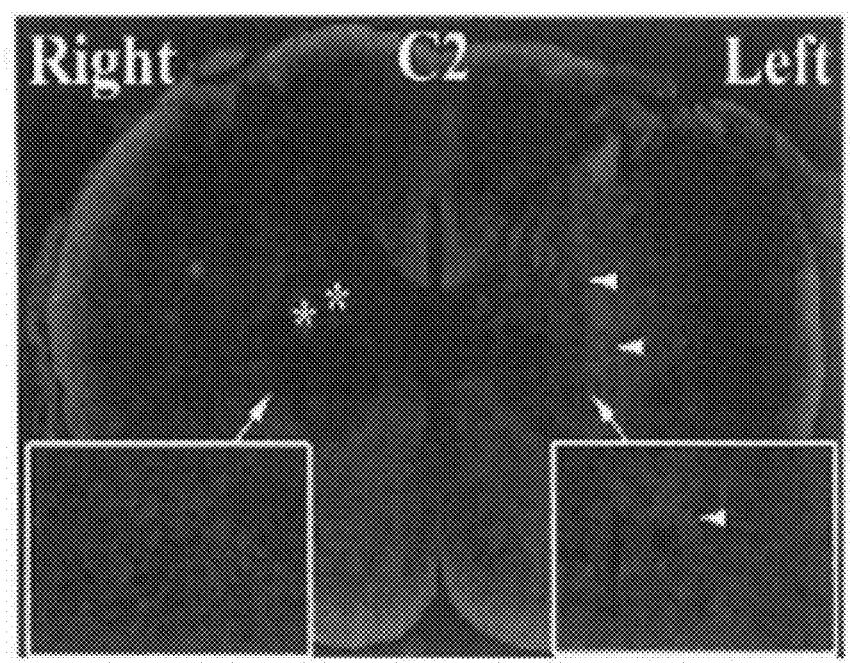
FIG. 6 is an image of the C2 cervical segment in a rabbit following EB staining. Dye was clearly seen within the capillaries (white arrows). Inserts are at 20×, indicating ventral horns on both sides of the cervical spinal cord. Asterisks mark the right side of the spinal cord.

Coronal tissue sections were cut at 30 µm in a cryostat, and dye distribution was analyzed, as seen in FIG. 6.

The data demonstrate selective delivery of EB dye into a discrete section of the non-injured rabbit cervical spinal cord. Minimally-invasive catheterization/isolation of the vertebral artery achieved direct dye delivery and distribution to distinct spinal cord regions while avoiding cerebral diffusion.

All referenced publications are expressly incorporated herein by reference, each in its entirety, to the same extent as if each were incorporated by reference individually. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A method for treating a neurological disorder characterized by spinal cord pathology in a patient in need thereof comprising:
    advancing a catheter into a spinal cord artery, wherein the catheter comprises a plurality of balloons disposed on a catheter shaft, at least one injection port disposed on the catheter shaft and between the plurality of balloons;
    guiding the catheter to a point distal to segmental spinal arteries so that at least one of the plurality of balloons is positioned distal to the segmental spinal arteries and at least another of the plurality of balloons is positioned proximal to the segmental spinal arteries;
    inflating the plurality of balloons to isolate a discrete region of a spinal cord to treat neurons affected by the neurological disorder;
    administering a therapeutically effective amount of a composition through the at least one injection port to the patient in need thereof, wherein the composition is a motor neuron therapeutic;
    allowing the composition to contact the affected neurons;
    deflating the plurality of balloons; and
    withdrawing the catheter;
    wherein the neurological disorder is selected from the group consisting of Amyotrophic Lateral Sclerosis (ALS), traumatic injury of the spinal cord, spinal cord stroke and perioperative spinal cord ischemia.

2. The method of claim 1, wherein the segmental spinal arteries are selected from the group consisting of cervical, thoracic and lumbar segmental spinal arteries.

3. The method of claim 2, wherein the plurality of balloons comprises two balloons that are disposed on the catheter shaft.

4. The method of claim 1, wherein the motor neuron therapeutic administered is stem cells.

\* \* \* \* \*